US008969073B2

(12) United States Patent
Heinrich (10) Patent No.: US 8,969,073 B2
(45) Date of Patent: Mar. 3, 2015

(54) DEVICE AND METHOD FOR ISOLATING CELLS, BIOPARTICLES AND/OR MOLECULES FROM LIQUIDS

(75) Inventor: Hans Werner Heinrich, Greifswald (DE)

(73) Assignee: pluriSelect GmbH, Leipzig (DE)

( * ) Notice: Subject to any disclaimer, the term of this patent is extended or adjusted under 35 U.S.C. 154(b) by 1274 days.

(21) Appl. No.: 11/699,914

(22) Filed: Jan. 30, 2007

(65) Prior Publication Data

US 2007/0190653 A1 Aug. 16, 2007

Related U.S. Application Data

(63) Continuation of application No. PCT/DE2005/001374, filed on Jul. 29, 2005, and a continuation of application No. PCT/DE2005/001371, filed on Jul. 29, 2005.

(30) Foreign Application Priority Data

Jul. 30, 2004 (DE) .................... 10 2004 037 476

(51) Int. Cl.
*C12M 1/00* (2006.01)
*C12M 1/34* (2006.01)
*C12M 1/36* (2006.01)
*C12M 3/00* (2006.01)
*G01N 33/50* (2006.01)
*G01N 1/40* (2006.01)

(52) U.S. Cl.
CPC .... *G01N 33/5002* (2013.01); *G01N 2001/4016* (2013.01)

USPC ............ 435/288.5; 435/2; 435/4; 435/283.1; 435/286.5; 435/287.1; 435/287.3; 435/287.5; 435/288.2; 435/288.4; 435/297.4; 435/297.5; 435/298.1; 435/308.1

(58) Field of Classification Search
CPC ............ B01L 3/50276; B01L 2200/00; B01L 2200/0647; B01L 2200/0652; B01L 2200/0668; B01L 2400/00; B01L 2400/04; B01L 2400/0487; B01L 2400/0622
See application file for complete search history.

(56) References Cited

U.S. PATENT DOCUMENTS

| 6,221,614 | B1* | 4/2001 | Prusiner et al. ............... 435/7.1 |
| 2003/0134416 | A1* | 7/2003 | Yamanishi et al. ............ 435/372 |
| 2004/0115278 | A1* | 6/2004 | Putz et al. ..................... 424/489 |
| 2004/0222144 | A1* | 11/2004 | Nakatani et al. .............. 210/435 |

* cited by examiner

*Primary Examiner* — Ja'Na Hines
(74) *Attorney, Agent, or Firm* — Buchanan Ingersoll & Rooney PC (57) ABSTRACT

The invention describes an appliance and a method, with the help of which specific bio-particles, but also dissolved bio-molecules can be recognized in and separated from fluids making use of suitable carriers and known immobilization methods. The appliance can be used both discontinuously and also for direct and continuous treatment of fluids. Fields of application of the invention are animals, bio-technology (including biological research) and medicinal diagnostics. Areas of application of the invention comprise, among others, therapy of humans, in particular direct treatment of blood.

14 Claims, 11 Drawing Sheets

Mouse-anti-Rat CD4 antibody coupled to PMA-particles, detected with Goat-anti-Mouse antibody labelled with the fluorescence-dye PE.

Figure 1:
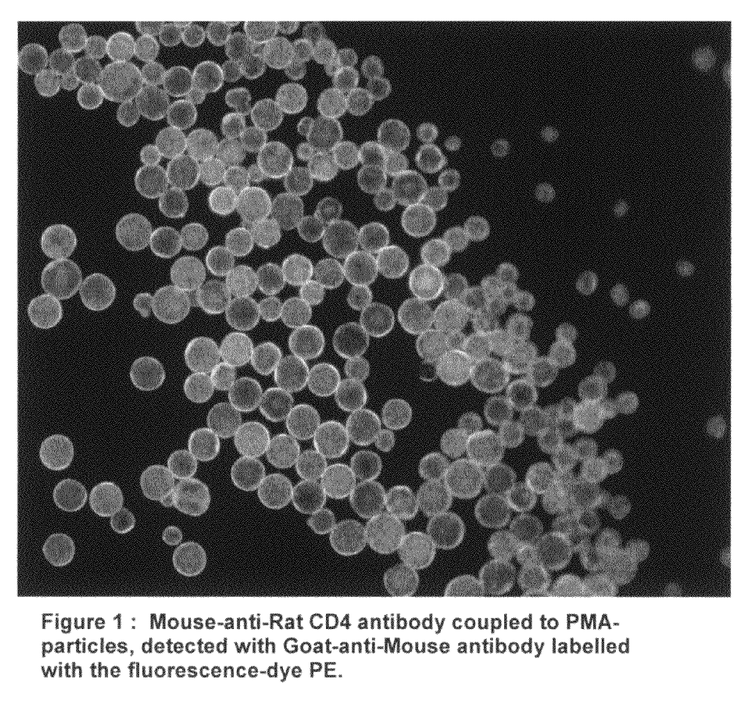

Figure 1 : Mouse-anti-Rat CD4 antibody coupled to PMA-particles, detected with Goat-anti-Mouse antibody labelled with the fluorescence-dye PE.

Figure 2:
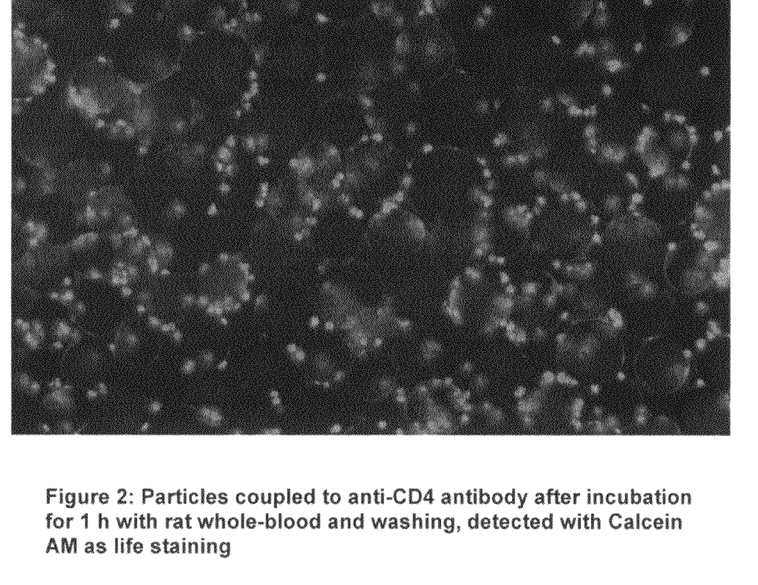

Figure 2: Particles coupled to anti-CD4 antibody after incubation for 1 h with rat whole-blood and washing, detected with Calcein AM as life staining Figure 3 : FACS-analysis, whole-blood cells before cell-isolation with activated PMA-particles labelled with anti CD4-FITC (FL1), lower left quadrant shows CD4-positive cells Figure 4 : FACS-analysis of whole-blood cells after cell-isolation of CD4-positive cells with activatd PMA-particles, labelled with anti-CD4-FITC (FL1), lower left quadrant shows CD4-positive cells Figure 5: FACS-analysis of cells dissociated from particles labelled with anti-CD4-FITC (FL1), lower left quadrant shows CD4-positive cells Fig. 6: PAGE cell-lysate without IgG, cell-lysate with IgG, isolated goat-IgG from citrate-buffer 1. cell-lysate before protein-purification
2. eluted proteins from sephadex-beads
3. eluted proteins from sephadex-beads
4. cell-lysate after protein-purification

Figure 7

Use of the device for the isolation of cells/particles/molecules from fluids (example: continous, blood)

Figure 8:
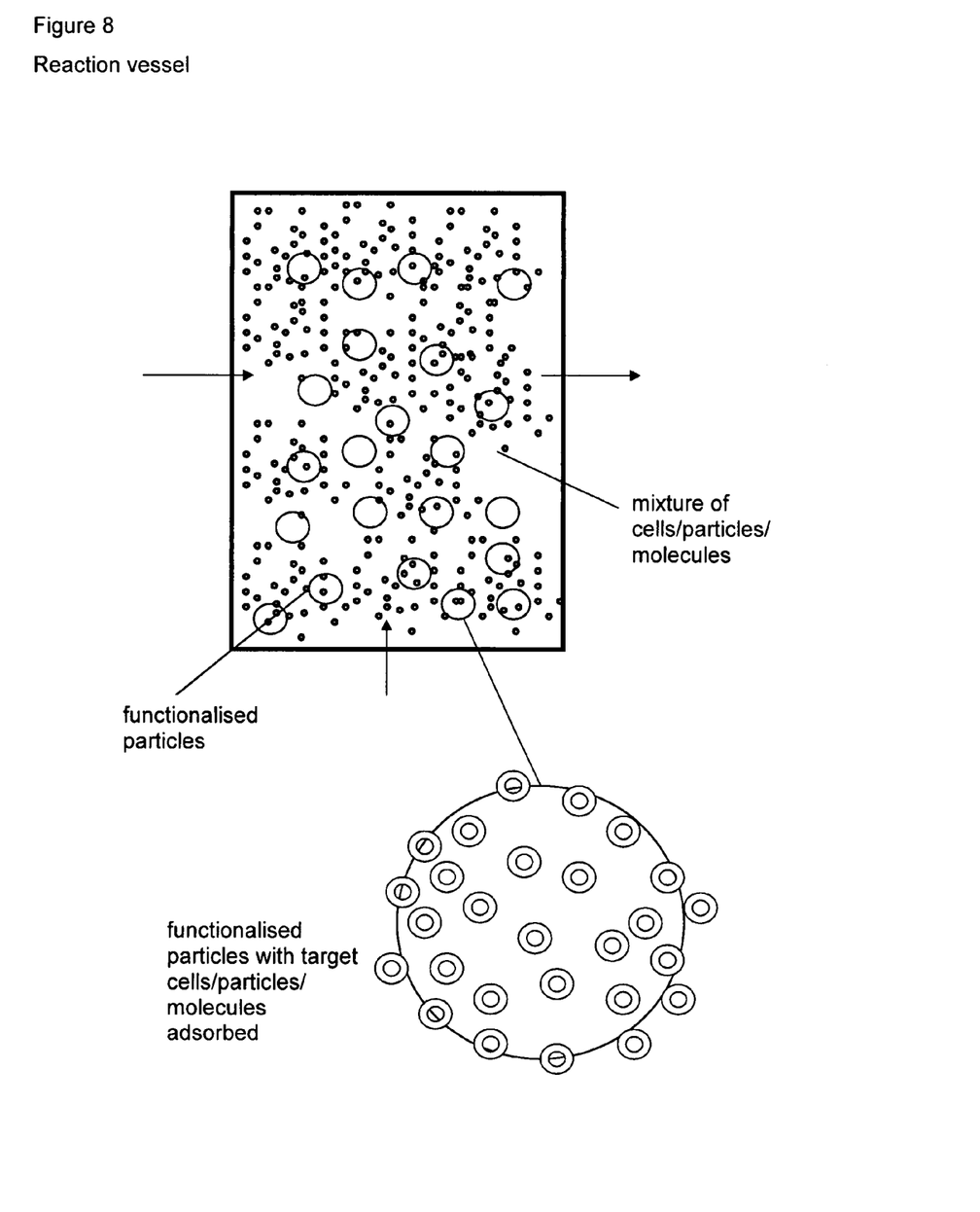

Figure 8
Reaction vessel

Figure 9:
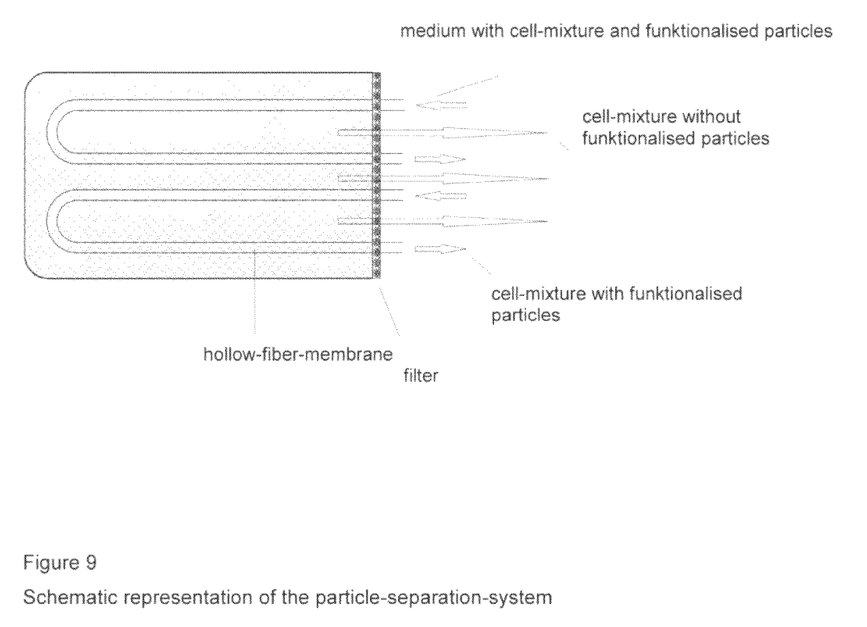

Figure 9
Schematic representation of the particle-separation-system

Figure 10:
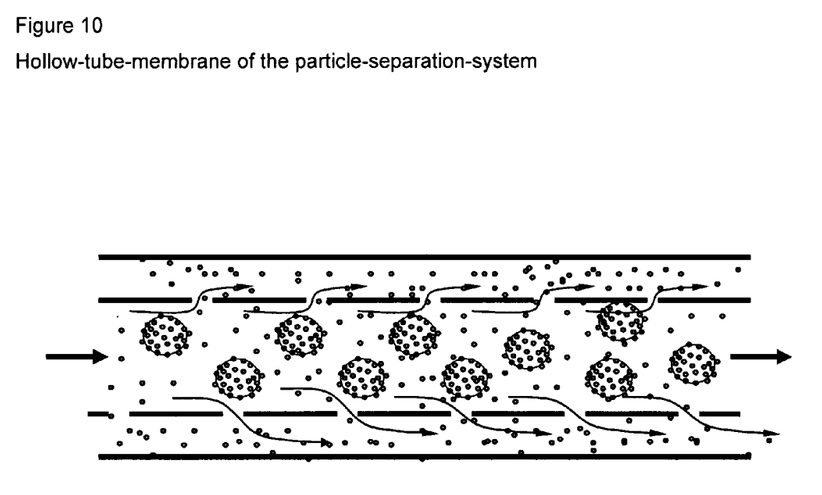

Figure 10
Hollow-tube-membrane of the particle-separation-system

Figure 11:
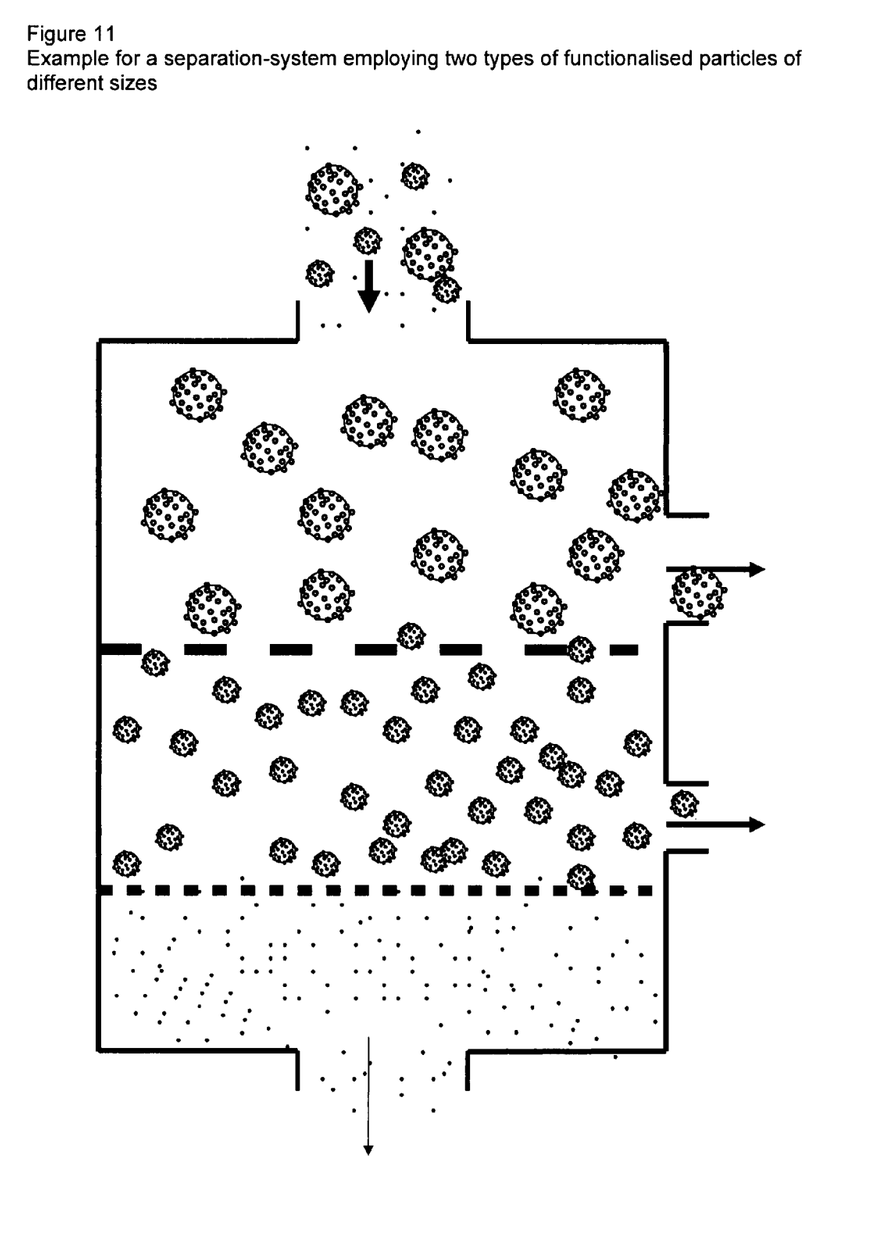

Figure 11
Example for a separation-system employing two types of functionalised particles of different sizes

DEVICE AND METHOD FOR ISOLATING CELLS, BIOPARTICLES AND/OR MOLECULES FROM LIQUIDS

This application is a continuation of International Application No. PCT/DE2005/001374 and PCT/DE2005/001371. Both applications were filed on Jul. 29, 2005 and were pending on the filing of this application. Both PCT applications claim priority to German Patent Application No. 10 2004 037 476.7, filed on Jul. 30, 2004 and pending on the day that the PCT applications were filed. Priority to that application is also claimed.

The invention describes an appliance and a method for the isolation of cells, bio-particles and/or molecules from fluids. With it and using suitable carriers and known immobilisation methods, specific bio-particles can be recognised and separated. Fields of application of the invention are the therapy of diseases of human beings, animals, biotechnology (including biological research) and medicinal diagnostics.

Despite significant success in the treatment of diseases, acute and chronic diseases caused by misguide of the immune system, still represent major challenges to doctors and medical research. There is a lack of influence on the course of diseases involving acute inflammation like sepsis or chronic diseases like allergies, auto-immune diseases but also tumor formation and the drugs that are applied frequently have significant side effects.

Growing insight into the regulation of innate and acquired immune system opens up new possibilities of purposeful manipulation of the immune system. Mainly this is achieved by administering drugs that, by blocking of a signalling-substance, interrupt specific mechanisms of regulation. Specific antibodies impede the effect of TNFa thereby preventing pro-inflammatory action of this cytokine by inactivating this molecule or blocking the cellular receptor. Among others rheumathoid arthritis can be treated successfully this way. Recombinant, activated Protein C (Drotrecogin Alfa, Xigris®) is used for purposeful intervention into the process of blood clotting (inhibition of factor Va and VIIIa, inhibition of Plasminogen-Activator-Inhibitor-1 and reduction of TAFI-synthesis), thus, allowing to reduce the death rate of patients suffering from severe sepsis significantly. More drugs are to be expected in the years to come. In the case of chronic diseases, in particular, the blocking substance has to be taken lifelong in most cases. Permanent prevention of an immune function that is vital, per se, has to be accompanied by side-effects. Preliminary experience with drugs of this kind lead to assume that specific diseases as tuberculosis are reactivated or get a chance to manifest this way at all.

Another possibility for therapeutic intervention resides in the removal of immune-regulating substances from blood by extra-corporal treatment of blood. Starting point for this development is classic venesection, that used to be the standard therapy for particular diseases for more than two-thousand years. New materials and technologies as well as research on blood types allowed introduction of hemo-dialysis for clinical application more than 50 years ago and resulted in blood-exchange therapy that was replaced by plasma-exchange later. Lack of specificity, costs and risk for infection limit the application of plasma-exchange.

Hemofiltration, hemodiafiltration, double-filtration and plasma-adsorption represent milestones in the application of extra-corporal therapeutic procedures. Plasmaadsorption allowed, for the first time, to remove substances from blood that are larger than albumin. Unspecific or specific factors are used for binding high molecular weight compounds in streaming blood or plasma. Today, routinely, LDL, Beta2-microglobulin, endotoxins, immunoglobulins and circulating immune-complexes are removed from blood applying electrostatic or hydrophobic interactions between matrix and blood components. Specific affinity of Protein A to the FC-receptor of IgG allowed to develop immune-adsorbers that are used for the depletion of IgG for the treatment of e.g. severe forms of rheumatoid arthritis (Prosorba®). Specific recognition sequences (antibodies, peptides) allow the removal of clearly defined specificities from blood. They are applied for eliminating LDL (Therasorb®, LDL Lipopak®), Lp(a) (Lp(a) Lipopak®), acetylcholin-receptor-antibody (MedisorbaMG®), anti-β1-adrenergic-antibody (Corafin®) or mediators of inflammation (EP 1163004).

Use of dissociated immuno-complex components derived from a patient as ligands for a patient-specific immune-adsorber (DE 19538641) is a special case on the track to more purposeful and personalized therapy. In addition to dissolved substances from blood plasma described above as targets of therapeutic apheresis, focus is increasingly shifting towards cells that can be isolated from blood for therapeutic approaches. Leukocyte-apheresis (Cytapheresis, Cellsorption) is used for unspecific removal of granulocytes as well as monocytes and lymphocytes from blood. The therapeutic application is advisable for a number of chronic diseases as e.g. Morbus Crohn.

Isolation of cells, bio-particles and/or molecules from fluids is of significance in many technical fields, numerous methods also being known for it.

Cell analysis and cell separation have been done by means of Fluorescence Activated Cell Sorting (FACS) for decades. It is the preferred method for the analysis of specific cell populations by surface markers. FACS application poses problems for the isolation of large numbers of cells, in particular for therapeutical application, The medium containing the cells must be highly diluted, the separation time is relatively long for larger quantities of cells and compliance with aseptic conditions causes problems. All told, the method causes considerable costs.

Magnetic separation methods have been increasingly used for recognition and isolation of bio-particles and cells for more than 10 years now. For this, either the trapping molecules are charged with iron or micro-particles containing a ferrous core are coated with the trapping molecule. The separation is done by a strong magnetic field. Immuno-magnetic separation, successfully commercialised inter alia by Dynal and Miltenyi Biotec, has established itself as a simple, relatively favourably priced method of cell separation. Particularly in comparison with Fow cytometry, magnetic separation has proven its worth for the isolation of relatively rare types of cells, for example for the isolation of foetal cells from the mother's blood for prenatal diagnostics. A further application is detection of tumour cells in blood after surgical removal of the primary tumour to initiate further treatments.

For therapeutic purposes, syngenic $CD34^+$-peripheral blood stem cells from patients suffering from certain malign diseases of the blood-forming system are nowadays routinely obtained for re-implantation. This is preferably done by the cleansing of leukocytes with specific antibodies coupled to magnetic beads. For cell fractioning during the blood/cell donation, a number of systems which make use of the varying size and specific density of the blood cells for a separation in the field of gravity (centrifugation) are available.

A disadvantage of all sorting methods is that they cannot be done continuously, that is to say that a blood or lymphocyte sample is taken, the cells are incubated with the immuno-magnetic particles. After separation and washing, the cells are split from the magnetic particle and can then be used for therapeutic purposes.

A good overview of FACS and MACS is given in "Fow Cytometry and Sorting" (Ed. Melamed et al., Wiley & Sons, Inc., New York, 1990).

Other methods of isolation and/or removal of cells are described in EP 12311956A2, U.S. Pat. No. 6,900,029, U.S. Pat. No. 6,432,630, US 20020012953A1, DE 10022635A1, U.S. Pat. No. 5,246,829, U.S. Pat. No. 5,739,033, U.S. Pat. No. 5,763,203, EP 0016552A1, WO 00/38762, EP 0502213B1 and EP 0554460B1.

U.S. Pat. No. 6,039,946 discloses a system for the removal of molecules (LDL, AFP) from fluids (blood, plasma). This system comprises two reaction-chambers, wherein one reaction-chamber contains the separation-mixture, from which biomolecules diffuse through semi-permeable membranes (cut off 0.001-0.01 µm) into the second reaction-chamber comprising functionalised particles. A disadvantage of this system resides in the fact, that separation/adsorption is not effected directly by contacting the fluid comprising particles (blood) with the immobilized ligand (chelating resin or antibody), but after previous compartmentalisation of (blood-)cells from molecule-solution (plasma) via semipermeable membranes or encapsulation of ligands respectively. As a result of separation according to U.S. Pat. No. 6,039,946 biomolecules are present as a mixture bound or eluted. Another disadvantage resides in the fact that this system does not allow to separate cells and subcellular particles from fluids. Further, from Ameer et al. (A novel immunoadsorption device for removing beta2-microglobulin from whole blood. Kidney Int 59 1544-50 (2001)) and Ameer et al. (Regional heparinization via simultaneous separation and reaction in a novel Taylor-Couette flow device. Biotechnol Bioeng 63 618-24 (1999)) modified Taylor-Coutte systems for the separation of molecules are known. Separation, however, similarly to U.S. Pat. No. 6,039,946, takes place after diffusion of target-molecules through a semipermeable membrane (cut off 1 µm) into the adsorption-compartment via movement of blood between two cylinders. The immobilized ligand is located in the adsorption-compartment. Separation/Adsorption is not effected directly by contact of fluid comprising particles (blood) with the immobilized ligand but after previous compartmentalisation of (blood-)cells from molecule-solution (plasma). Thus, no cells or subcellular particles can be removed from the fluids. Progressing insight into the importance of blood-cell sub-populations for regulating the defence against pathologic processes in general opens up possibilities for manipulating the immune-system in the sense of maintaining homeostasis of the organism. This helps to establish new approaches for patient-specific therapy of diseases. Thus an effect is achieved by removing specific "pathologic" blood-cells, including infected cells, as well as by isolating blood-cell subpopulations, their ex-vivo treatment and return into the organism. This kind of extra-corporal, patient- and disease-specific treatment requires a simple system for isolating cells from blood.

The problem solved by the present invention resides in providing a basic system for separating cells, bioparticles and molecules, that is useful for efficient and economic therapy, based, in particular, on the removal of detrimental substances from human body fluids, e.g. blood, and which, further, can be applied for separating cells, bioparticles and molecules from animal body fluids or can be applied in biotechnology including biological research as well as medical diagnostics.

The invention describes a simple separation method which can be used wherever a specific ligand can functionally be immobilised onto a surface for the agent of a mixture of substances to be separated. The actual separation is done through sorting by particle size (filtration, screening).

For the solution of this task, standard methods of coupling of specific ligands to a solid carrier are used.

The solid carriers used are known biopolymers such as membranes or particles from organic or synthetic polymers. The surface can be biocompatible and comprise collagen, cleansed proteins, cleansed peptides, poly-saccharides such as chitosan, alginate, dextran, cellulose, glycosaminoglycanes or synthetic polymers such as polystyrene, polyester, polyether, polyanhydride, polyalkylcyanoacrylate, polyacrylamide, polyorthoester, polyvinyl acetate, block copolymers, polypropyls, polytetrafluoroethylene (PTFE) or polyurethane. Over and above this, the polymers can contain lactic acid polymers or copolymers (lactic acid and/or glycol acid (PLGA).

The surfaces used can be biodegradable or non-biodegradable.

The specific ligands used for the binding of the target molecules on the surface of cells can be natural or of a synthetic nature, for example antibodies, antibody fragments, peptides, polypeptides, glycopeptides, soluble receptors, steroids, hormones, mitogens, antigens, superantigens, growth factors, cytokines, leptins, virus proteins, adhesion molecules or chemokines.

For the specific use, at least one antibody or antibody fragment is used, with the specific ligands being covalently bound to them or fixed to them via spacers or linkers.

The carrier substance can manifest arbitrary geometry. Membranes as capillaries or particles provide the advantage of a large surface. For the method to be described, microparticles with a diameter of >10 µm<800 µm, preferably 50-500 µm are used. For other tasks, larger or smaller particles can also be used.

The micro-particles activated with specific ligands (e.g. antibodies against CD34 or CD1d, or against HIV-gp120) are put into contact ex vivo with obtained blood, which is treated with customary anti-coagulants. This is done in a separate reaction area. If the reaction area is to be placed in an extracorporal circulation, hose connections, valves, filters and pumps connected to the securing technique ensure that the system can be operated without side-effects for the patients following corresponding anti-coagulation.

The target cells are bound by the functionalised microparticles. The separation of the micro-particles, which are now charged, is done by hydrostatic pressure making use of a membrane (screen), preferably in the shape of a tube which allows all the blood components to pass without obstacles (pore size >10 µm<800 µm), but retains the micro-particles. Filtration can be done by both vertical and also tangential effects of pressure. The particles remaining in the lumen are fed back to the reaction vessel or guided off for analytical or preparative purposes. For instance, the blood depleted in this manner from defined cells is returned to the donor/patient via the arm vein.

After stopping the flow of blood, the reaction vessel can be used for separation of the cells from the micro-particles. The dispersed cells separated in this way can be removed from the particles by means of the same process and are now available for diagnostic applications.

A further application is purposeful isolation of various cell types with the objective of co-cultivation whenever the cell types in question need surface molecules and/or bio-molecules like cytokines of other cell types in order to fulfill their required function.

To achieve sufficient proximity of the required target cells for the necessary cell-cell contact, a number of specific ligands can be bound on one particle.

Specific cells for this application can, inter alia, be T-cells, B-cells or stem cells.

The great number of properties of particles that can be varied, including material, size and surface modification, results in a large variety of applications with respect to medicine, animals, medical diagnostics as well as in biotechnology and biological research. The process can be performed in a discontinous as well as in a continuous manner.

The invention, thus, in principle, describes a system comprising mobile micro-particles, in particular for the separation of cells and subcellular particles from fluids, as well as uses of this system. It comprises two or more reaction-chambers separated by one or several membranes/filters of different mesh size (1-1000 µm) permeable for molecules of any size-range. As shown in the examples describing the apparative realisation (e.g. example 3, FIGS. 7-11) the apparatus according to the present invention comprises a reaction-chamber consisting of biocompatible material, comprising a mixture of cells, particles and molecules, functionalised micro-particles that recognize and bind the desired cells, bioparticles and/or molecule-populations, wherein micro-particles are freely mobile and can be transferred from the reaction-chamber to a particle-separation-chamber, a particle-separation chamber based on one or several membranes/filters with pores allowing passage of cells, bio-particles and/or molecules but not micro-particles for the separation of a medium with a cell-mixture and micro-particles via hydrostatic pressure into a cell-mixture with micro-particles and a cell-mixture without micro-particles, or for the separation of a medium with a cell-mixture and micro-particles via hydrostatic pressure into a cell-mixture with free micro-particles not bound to cells on one side of the membrane and into a medium on the other side of the membrane, comprising only specific complexes of functionalised micro-particles and target-cells, a filter/hollow-fiber-membrane, wherein the membrane has a pore size that allows passage of the cell-mixture without micro-particles only, optionally a pump for pumping/transferring fluid via a valve into the reaction-chamber, a valve via which fluid is pumped/transferred into the reaction-chamber, a valve via which the cell-mixture without micro-particles is pumped/transferred into the reaction-chamber, a tube-system for transferring or pumping fluids comprising a cell-mixture via a valve into a reaction-chamber comprising functionalised micro-particles, and for transferring of medium with cell-mixture and functionalised micro-particles from the reaction-chamber over a filter comprising a hollow-fiber-membrane for separating the medium into a cell-mixture without functionalised micro-particles and into a cell-mixture with functionalised micro-particles or for transferring the medium with cell-mixture and functionalised micro-particles from the reaction-chamber over a filter for separating the medium into a cell-mixture with free micro-particles not bound to cells on one side of the membrane and into a medium on the other side of the membrane comprising only specific complexes comprising functionalised micro-particles and target cells and for transferring the separated cell-mixture without functionalised micro-particles via a valve and for transferring the separated cell-mixture comprising functionalised micro-particles and the cells/bioparticles/molecules bound thereto to the reaction-chamber or for transferring the cell-mixture comprising the functionalised micro-particles and the cells/bioparticles/molecules bound thereto for analytical or preparative purposes, as well as for continuous-use a number of tube-systems, membranes, pumps and valves for performing all operations with respect to isolation, singling, processing and separation of cells, bioparticles and/or molecules.

Particularly suitable for a number of different requirements is e.g. a device according to the invention for isolating cells or bioparticles alone or in combination with molecules wherein only one filter and one particle size is used.

In particular devices proved to be of value wherein micro-particles are functionalised with a specific ligand, covalently bound or fixed to them via a spacer or linker.

In a preferred embodiment micro-particles are solid carriers with a surface consisting of polymetacrylate, polyalkylcyanoacrylate, polysulfone, polyacrylonitrile, polmethylmethacrylate, polyvinyl-alcohol, polyamide, polycarbonate or a cellulose-derivative (e.g. sepharose), wherein sepharose is particularly preferred, or consisting of a combination of these materials.

In particular devices according to the invention proved to be of value wherein the hollow-fiber-membrane was formed as a hollow-tube-membrane.

The method of the invention, for which the device comprising microparticles that can move freely between the reaction-chambers is particularly suitable, comprises, as shown in the examples and the figures, pumping or transferring, via a valve, fluid comprising cells, into a biocompatible reaction-chamber that comprises functionalised microparticles, that, optionally, interact in the mixture with components of the fluid. The medium comprising cell-mixture and functionalised microparticles is transferred from the reaction-chamber into a particle-separation-system comprising filter and hollow-fiber membrane, wherein the membrane has a pore-size allowing passage of cell-mixture without functionalised particles only, so that the medium with cell-mixture and functionalised particles is separated into a cell-mixture with functionalised particles and a cell-mixture without functionalised particles by hydrostatic pressure with the filter and the hollow-fiber membrane. After that, the separated cell-mixture without functionalised particles is transferred from the particle-separation-system via a valve and the cell-mixture with functionalised particles as well as, if applicable, target cells/bioparticles/molecules bound thereto, are transferred to the reaction-chamber or transferred for preparative purposes. Thereby, for example, use of particles functionalised in different ways and having different sizes, that allow simultaneous separation and isolation in different compartments by "fractionated filtration", is possible, according to the invention.

The method according to the invention is used in this respect in particular directed at applications related to the treatment of human diseases, animals, biotechnology (including biological research) as well as medical diagnostics.

In a particularly preferred embodiment of the invention ligand or ligands are coupled to solid carriers, in particular microparticles comprising a surface comprising polymetacrylate, polyalkylcyanoacrylate, polysulfone, polyacrylonitrile, polmethylmethacrylate, polyvinyl-alcohol, polyamide, polycarbonate or a cellulose-derivative (e.g. sepharose), wherein sepharose is particularly preferred, or to a combination of these materials.

Particularly suitable are methods employing reaction-chambers with particles functionalised in different ways comprising separation-modules with membranes/filters of different pore-sizes in various numbers, connected in series and/or comprising pumping of the fluids with a pump into the reaction-chamber.

For a number of different applications particularly suitable are methods wherein cells, bioparticles and/or molecules are dissociated from the microparticles by applying specific buffers, e.g. by pH-shift, e.g. by applying acidic or basic solutions and/or a detergent.

For example, the method is suitable as well when separated cells, bioparticles and/or molecules are used for analytic procedures and/or further processing without the intention to apply it to humans.

Further, the method has proven useful as well when separated cells, bioparticles and/or molecules were transferred into animals in unprocessed or modified form, with the intention of researching or treating diseases In particular, method and device of the invention are suitable for purification, enrichment or depletion of cells, bioparticles and/or molecules for diagnostics or further processing.

For a number of different applications method and device of the invention proved to be useful, wherein the hollow-fiber membrane was a hollow-tube membrane, so that functionalised particles comprising cells/bioparticles/molecules separated from the blood remain within the extra-corporal cycle comprising the hollow-tube system.

Thus, in particular the invention relates to a system comprising mobile microparticles, in particular for separating cells and subcellular particles from fluids. It comprises two or more reaction-chambers, separated by one or more membranes/filters of different pore sizes (1-1000 µm) and permeable for molecules of any size range. This, for example, allows the use of particles that are functionalised in different ways and have different particle sizes, thereby allowing simultaneous separation and isolation into different compartments by "fractionated filtration".

Thus, in principle, the invention is a system for isolating cells and subcellular particles alone or in combination with molecules, wherein a mixture of binder-particles having different sizes can be used. Thus, for the first time, this allows modular enrichment, in particular of cells and subcellular particles, by cascade-filtration with the intention of singling-out the mixture of binding-particles.

EMBODIMENT 1

Isolation of CD4-Positive Cells from Whole Rat Blood

Ascitis antibodies (RIB 5/2) were carried out according to the protocol with the help of Millipore Montage Antibody Purification Kit (LSK2 ABG 20).

Purification was subsequently checked with an SDS denaturising gel (10%).

Coupling of the Anti-CD4 Antibodies to the Polymethylacrylate (PMA) Particles 1. 1 ml PMA (particle diameter=40 µm+/−10 µm; 10 mg/ml; COOH/PEG-COOH modified) centrifuged for 2 min 3,000×g, reject supernatant and absorb in 1 ml 0.1M MES buffer pH 6.3.
2. Dissolve 2 mg EDC and 2.4 mg N-hydroxysuccinimide in 0.5 ml 0.1M MES buffer pH 6.3 and add to the PMA particle suspension. Incubate for 1 hour at room temperature, stirring (activation of the particles).
3. Separate PMA particles by centrifugation and wash twice with 0.1M MES buffer pH 6.3.
4. Absorb activated PMA particles in 1 ml 0.1M MES buffer pH 6.3 with 100-150 µg antibodies; coupling reaction at room temperature for 16 hours (overnight).
5. Neutralisation of free binding points by addition of 100 µl 1M ethanolamines with subsequent incubation for 1 hour.
6. Separation by means of centrifugation and washing of the functionalised PMA particles with PBS 3 times.
7. Absorption of the anti-CD4 PMA particles in 1 ml PBS pH 7.4 and storage at 4° C. Check of the antibody coupling by means of Goat anti-mouse antibodies, PE marked (FIG. 1).

Figure 3:
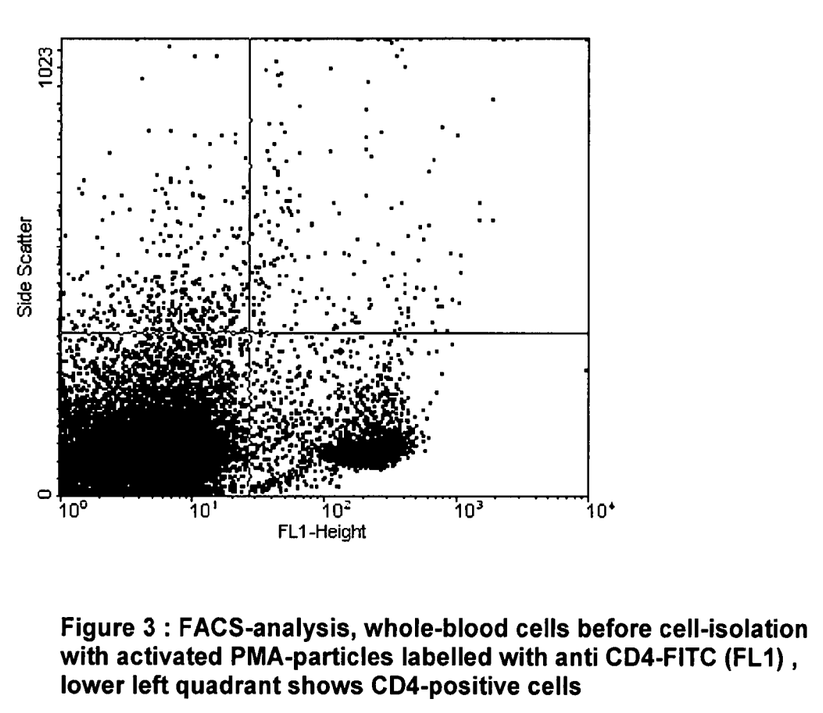
Figure 4:
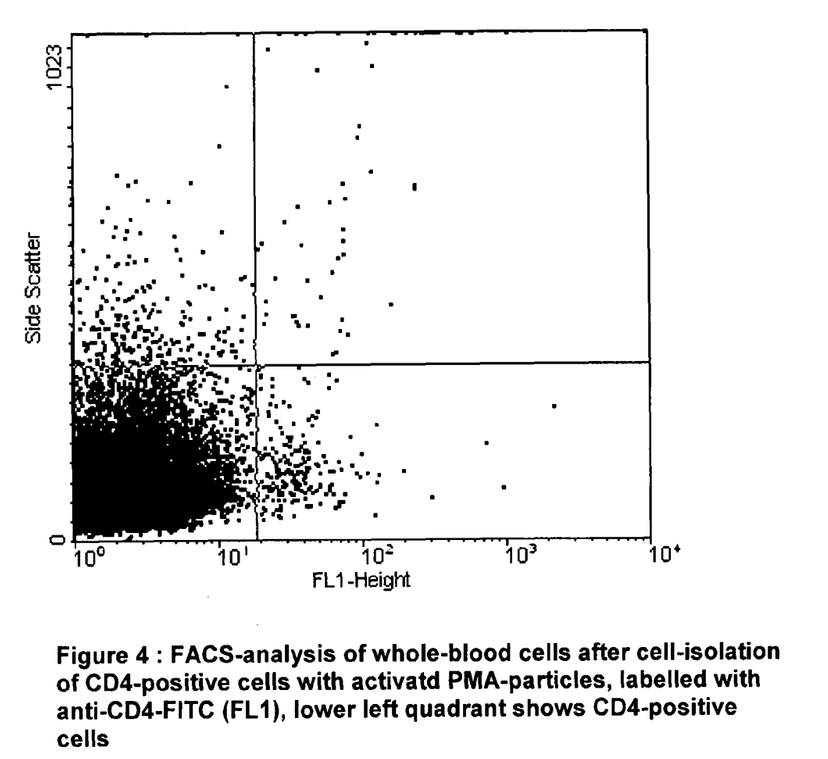

Specific Cell Isolation from CD4 Positive Cells from Full Blood 1. 4 ml anti-coagulated full rat blood is mixed with 1 ml (1 mg particles) of functionalised anti-CD4 PMA particle suspension.
2. Incubate rocking at room temperature for 60 min.
3. Separation of the anti-CD4 PMA particles (with and without bound cells) from the full blood by filtration of the blood particle mixture by means of a specific chamber with a cell screen (40 µm).
4. Washing of the anti-CD4 PMA particles with 30 ml PBS (1% FCS)
5. Absorption of the particles from the screen chamber in approx. 1 ml PBS, vortex (mix) for 15-20 seconds.
6. Removal of a particle sample for microscopic analysis (FIG. 2).
7. FACS analysis of the leukocyte fraction in the full rat blood before and after the treatment with the anti-CD4 PMA particles (FIGS. 3 and 4).

Separation and Qualification of the Cells from the Particles.

Figure 5:
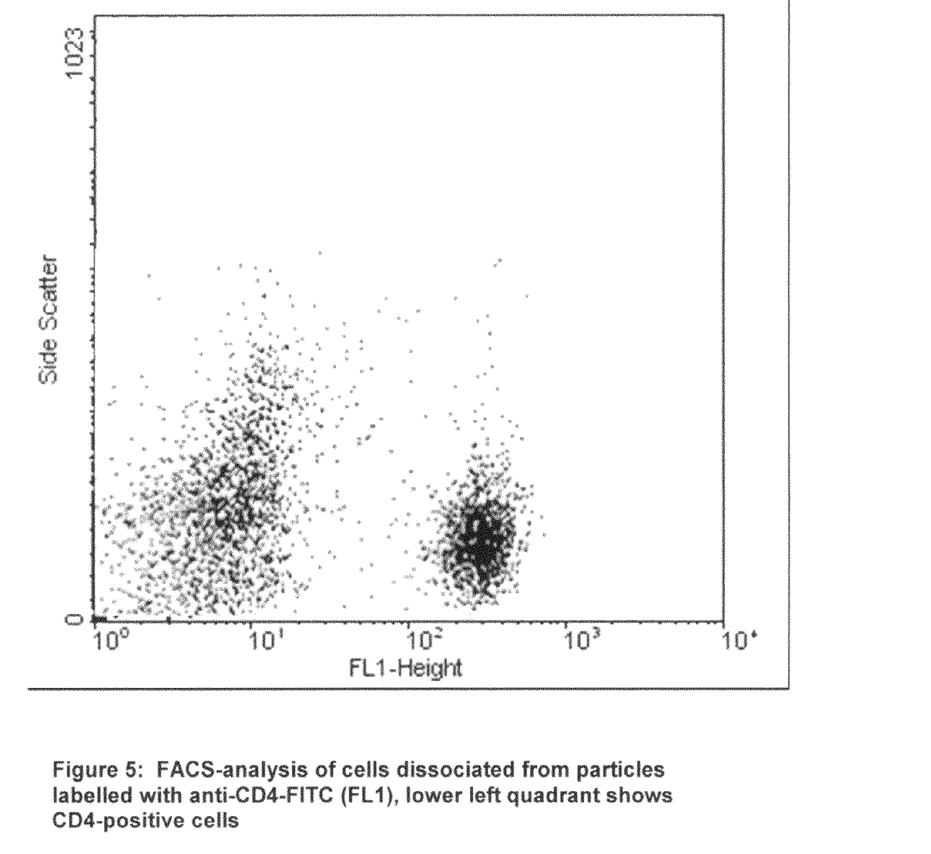

1. Anti-CD4 PMA particles of the adhering cells are sedimented by careful centrifugation.
2. Absorption of the sediment in PBS, 2 mM EDTA, 3 mM mercaptoethanol and 20 U Papain.
3. Incubation with mixing for 30 min.
4. Separation of cells and particles by a filtration by means of a specific chamber with a cell screen (40 µm); washing of the particles with 30 ml PBS (1% FCS); absorption of the particles from the cell screen in approx. 1 ml PBS; vortex (mix) for 15-20 seconds and repetition of the washing.
5. Concentrate the isolated lymphocyte fraction by centrifugation 350×g and analyse by means of FACS (FIG. 5).

EMBODIMENT 2

Isolation of a Protein (IgG) from a Cell Lysate

Ascitis antibodies (RIB 5/2) were carried out according to the protocol with the help of Millipore Montage Antibody Purification Kit (LSK2 ABG 20).

Purification was subsequently checked with an SDS denaturising gel (10%).

Coupling of the (Mouse-IgG$_2$) Anti-CD4 Antibodies to the Polymethylacrylate (PMA) Particles 1. 1 ml PMA (particle diameter=40 µm+/−10 µm; 10 mg/ml; COOH/PEG-COOH modified) centrifuged for 2 min 3.000×g, reject supernatant and absorb in 1 ml 0.1M MES buffer pH 6.3.
2. Dissolve 2 mg EDC and 2.4 mg N-hydroxysuccinimide in 0.5 ml 0.1M MES buffer pH 6.3 and add to the PMA particle suspension. Incubate for 1 hour at room temperature, stirring (activation of the particles).
3. Separate PMA particles by centrifugation and wash twice with 0.1M MES buffer pH 6.3.
4. Absorb activated PMA particles in 1 ml 0.1M MES buffer pH 6.3 with 100-150 µg antibodies; coupling reaction at room temperature for 16 hours (overnight).

5. Neutralisation of free binding points by addition of 100 µl 1M ethanolamines with subsequent incubation for 1 hour.
6. Separation by means of centrifugation and washing of the functionalised PMA particles with PBS 3 times.
7. Absorption of the mouse-IgG PMA particles in 1 ml PBS pH 7.4 and storage at 4° C. Check of the antibody coupling by means of Goat anti-mouse antibodies, PE marked (FIG. 1).

Specific Isolation of Goat Anti-Mouse IgG from a Cell Lysate
1. 1 ml cell lysate (HepG2, 4×10⁶) is mixed with 1 mg Goat anti-mouse-IgG.
2. 0.1 ml (100 µg particles) of functionalised mouse-IgG PMA particle suspension is added to the protein mixture.
3. Incubate rocking at room temperature for 60 min.
4. Separation of the mouse-IgG PMA particles (with and without the bound Goat anti-mouse-IgG) from the cell lysate by filtration by means of a specific chamber with a screen membrane (10 µm).
5. 3× washing of the PMA particles with 5 ml PBS each time.

Figure 6:
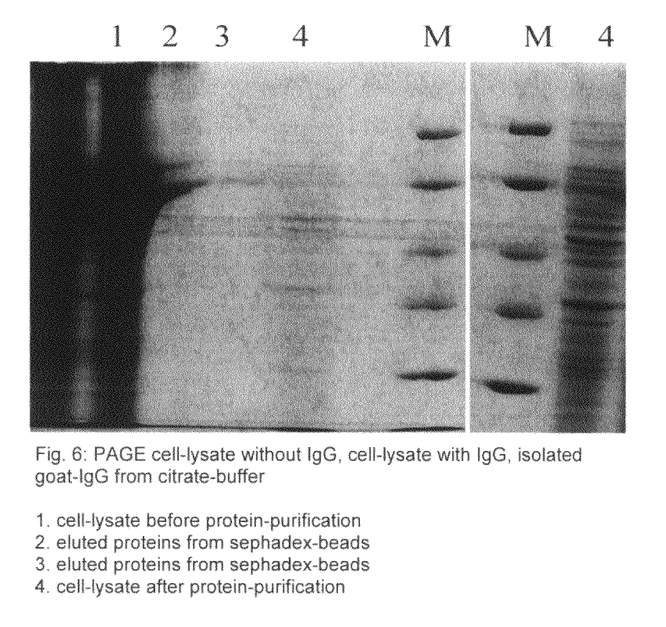

Separation and Qualification of the Protein from the Particles.
1. Absorption of the functionalised PMA particles with the adhering proteins from the screen chamber in 0.5 ml citrate buffer pH 2.2; incubation for 30 min.
2. Separation of the particles by filtration by means of a specific chamber with a screen membrane (10 µm); washing of the particles with 2 ml citrate buffer.
3. Analyse separated proteins in citrate buffer (FIG. 6).

EMBODIMENT 3

Figure 7:
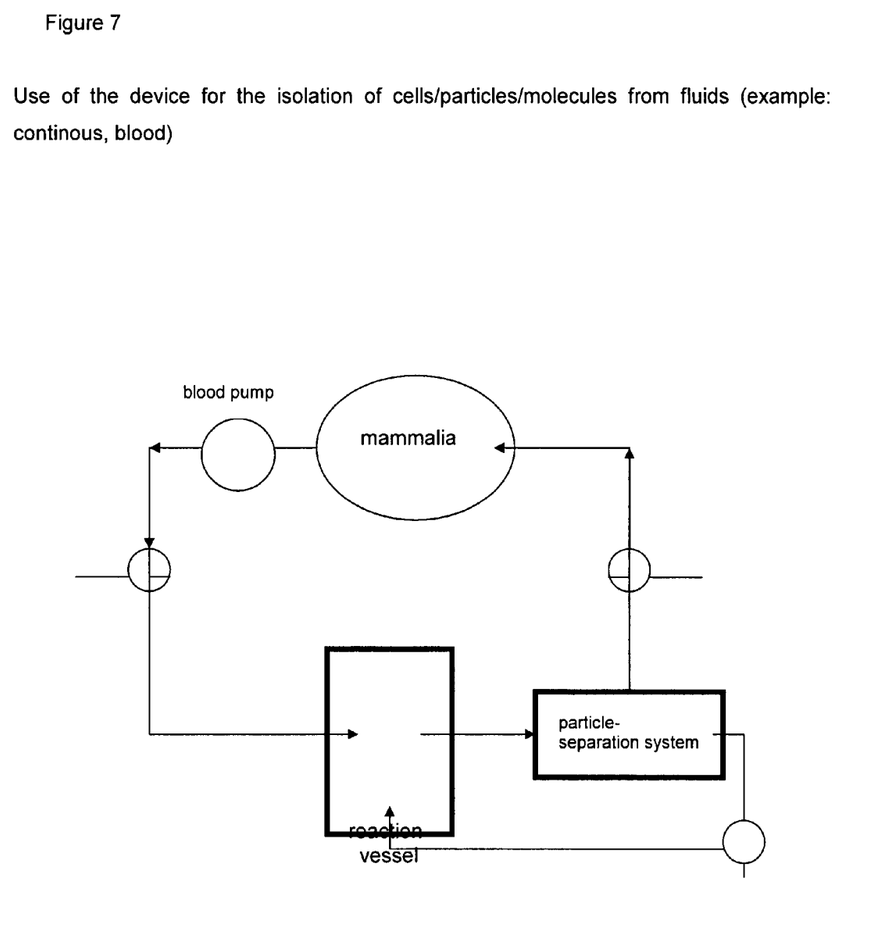

FIGS. 7-11 show examples of apparatus-based realisation of the invention or of parts thereof, as the case may be. FIG. 7 shows a system which is typically applicable for continuous use. Dotted arrows represent the hose system, arrow tips mark the direction of flow of the fluid. Starting from the organism (mammals), body fluid, for example blood, is pumped or guided into a reaction vessel containing functionalised particles, which possibly interact with components of the body fluid in a mixture, via a blood pump and a valve (marked in a circle in the illustration (FIG. 8). The medium with a cell mixture and functionalised particles is then guided into a particle separation system. According to one example, the medium with cell mixture and functionalised particles is guided across a screen and across a hollow-fibre membrane and separated into a cell mixture without functionalised particles and a cell mixture with functionalised particles (FIG. 9). Whereas the diminished-concentration mixture without functionalised particles is guided off via a valve and fed to the organism, the cell mixture with functionalised particles and the target cells/bio-particles/molecules bound onto them is fed back to the reaction vessel (FIG. 7). FIG. 10 exemplarily shows the principle of separation within the hollow-fibre membrane. The medium with cell mixture and functionalised particles is guided through a hollow-tube membrane, the latter being equipped with a pore size (dotted line) which merely permits passage of the cell mixture, now essentially no longer containing the target cells/bio-particles/molecules, whereas the functionalised particles with the separated target cells/bio-particles/molecules remain in the interior of the hollow-tube system.

FIG. 11 portrays a detail of a corresponding particle separation system which can be used for two types of functionalised particles with differing diameters.

All features, alone as well as in combination, disclosed in the preceding description, the following claims and the figures can be relevant for realizing the invention in its different embodiments.

The foregoing description of preferred embodiments of the invention has been presented for the purposes of illustration and description. It is not intended to be exhaustive or to limit the invention to the precise form described, and many modifications and variations are possible in light of the teaching above.

The embodiments were chosen and described in order to best explain the principles of the invention and its practical applications to thereby enable others skilled in the art to best utilize the invention in various embodiments and with various modifications as are suited to the particular use contemplated. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. An appliance for the isolation of target cells from blood with the objective of an application for the treatment of human diseases, for animals, in bio-technology and medicinal diagnostics, comprising:
   a reaction vessel of biocompatible material, in which blood is situated, wherein the blood comprises target cells,
   functionalised micro-particles having a diameter greater than 10 µm and less than 800 µm, which recognise and bind target cells, the micro-particles having the same or different fractional sizes, said micro-particles are freely mobile and able to be guided from the reaction vessel to a particle separation system,
   a particle separation system based on two or more membrane/screen/sieves forming a sieve cascade with pores having a size greater than 10 µm, less than 800 µm, and less than the diameter of the smallest fraction of functionalised micro-particles, which allow the cells, but not the micro-particles to pass, for separation of a medium with a cell mixture and micro-particles by hydrostatic pressure into a cell mixture with free micro-particles not bound to cells beyond the membrane and specific complexes from functionalized smallest fraction of micro-particles and target cells into a medium on the opposite side of the membrane, only containing the specific complexes from functionalised micro-particles and larger than the smallest fraction of target cells,
   a screen/hollow-fibre membrane, the latter equipped with a pore size merely permitting the passage of the cell mixture without micro-particles,
   a pump in order to pump/guide fluid into the reaction vessel via a valve,
   a valve, via which the fluid is pumped/guided into the reaction vessel,
   a valve, via which the cell mixture without micro-particles is guided off from the particle separation system,
   a hose system for (A) guiding or pumping of fluid with a cell mixture into a reaction vessel containing functionalised micro-particles via a valve and (b) guiding the medium with cell mixture and functionalised micro-particles from the reaction vessel via a screen/sieve or with a hollow-fibre membrane for separation of the medium into a cell mixture without functionalised micro-particles and into a cell mixture with functionalised micro-particles or to guide the medium with cell mixture and functionalised micro-particles from the reaction vessel via a screen/sieve for separation of the medium into a cell mixture and specific complexes from functionalized smaller-fraction micro-particles and target cells and with free micro-particles not bound to cells beyond the membrane and into a medium on this side of the membrane which only contains the specific complexes from functionalised micro-particles and target cells and (C) to guide off the separated cell mixtures without functionalised micro-particles via a valve and (D) to guide the separated cell mixtures with the functionalised micro-particles and the cells bound to it back to the reaction vessel or to guide off the cell mixture with the functionalised micro-particles and the cells bound to it for analytical or preparative purposes, and, for continuous use, various hose systems, membranes, pumps and valves, in order to be able to carry out all the actions of isolation, separation, processing and removal of the cells.

2. The appliance of claim 1 for isolation of target cells, wherein only screens with one pore size and functionalized micro-particles which have the same diameter are used.

3. The appliance of claim 1, wherein the micro-particles are functionalised with a specific ligand which is bound to them covalently or is fixed to them via a spacer or via a linker.

4. The appliance of claim 1, wherein the target cells are somatic cells and the fluid is blood.

5. The appliance of claim 1, wherein said functionalized microparticles are of at least two different diameters.

6. The appliance of claim 5, wherein said functionalised micro-particles bear more than one specific ligand and thus two and more differing target cells, bind to the micro-particles, and optionally wherein a cell-stimulating function for living cells can take place via the additional ligand(s), and optionally, wherein at least two differing cell types leading to the stimulation of at least one cell type by membrane/mediator interaction are separated via the additional ligand(s).

7. The appliance of claim 1, wherein the functionalised micro-particles are suspended in the fluid and are freely mobile, wherein the suspension of functionalized micro-particles is optionally accomplished by mechanical effects, and optionally wherein the fluid from the reaction area provided with the micro-particles is freed of micro-particles by filtration.

8. The appliance of claim 1, wherein membranes excelling through pores with a diameter which permits all components not specifically adsorbed, but not the used micro-particles, to pass through are used for the filtration.

9. The appliance of claim 1, wherein the micro-particles are solid carriers with a surface selected from the group consisting of polymetacrylate, polyalkylcyanoacrylate, polysulfone, polyacrylonitrile, polmethylmethacrylate, polyvinyl-alcohol, polyamide, polycarbonate and sepharose.

10. The appliance of claim 1, wherein the membrane is designed as a hollow-tube membrane.

11. The appliance of claim 1, wherein said functionalized microparticles are a mixture of microparticles functionalized in different ways and having different sizes.

12. The appliance of claim 1, wherein said microparticles have a diameter greater than 50 μm and less than 500 μm.

13. The appliance of claim 3, wherein the specific ligands are antibodies.

14. The appliance of claim 1, wherein two or more functionalized microparticle specificities different in size are used simultaneously.

\* \* \* \* \*